(12) United States Patent
DiCarlo

(10) Patent No.: US 9,413,976 B2
(45) Date of Patent: Aug. 9, 2016

(54) AUTO EXPOSURE OF A CAMERA IN A SURGICAL ROBOT

(71) Applicant: INTUITIVE SURGICAL OPERATIONS, INC., Sunnyvale, CA (US)

(72) Inventor: Jeffrey DiCarlo, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 178 days.

(21) Appl. No.: 13/961,737

(22) Filed: Aug. 7, 2013

(65) Prior Publication Data

US 2014/0046341 A1 Feb. 13, 2014

Related U.S. Application Data

(60) Provisional application No. 61/681,090, filed on Aug. 8, 2012.

(51) Int. Cl.
| | |
|---|---|
| *H04N 5/235* | (2006.01) |
| *A61B 19/00* | (2006.01) |
| *A61B 1/045* | (2006.01) |
| *A61B 1/00* | (2006.01) |
| *H04N 5/225* | (2006.01) |

(52) U.S. Cl.
CPC .......... *H04N 5/2353* (2013.01); *A61B 1/00006* (2013.01); *A61B 1/045* (2013.01); *A61B 19/2203* (2013.01); *H04N 5/2351* (2013.01); *H04N 2005/2255* (2013.01)

(58) Field of Classification Search
CPC ................... A61B 2019/5265; A61B 19/2203; A61B 19/5212; A61B 19/5225; A61B 19/22; A61B 19/5244; A61B 1/00006; A61B 1/045; A61B 1/00009; H04N 5/2353; H04N 5/2354
USPC ......................................................... 600/180
See application file for complete search history.

(56) References Cited

U.S. PATENT DOCUMENTS

| | | | | |
|---|---|---|---|---|
| 5,091,779 | A * | 2/1992 | Ams ...................... | A61B 1/042 348/69 |
| 5,182,636 | A * | 1/1993 | Kikuchi et al. ............ | 348/225.1 |
| 5,880,782 | A * | 3/1999 | Koyanagi et al. ............. | 348/364 |
| 6,424,805 | B2 * | 7/2002 | Ohsawa .......................... | 396/50 |
| 7,492,391 | B1 * | 2/2009 | Kaplinsky .................. | 348/218.1 |
| 2002/0070278 | A1 * | 6/2002 | Hung et al. ............... | 235/472.01 |
| 2003/0112360 | A1 * | 6/2003 | Liao et al. ..................... | 348/362 |
| 2006/0044459 | A1 * | 3/2006 | Kato ............................. | 348/362 |
| 2006/0165288 | A1 * | 7/2006 | Lee et al. ...................... | 382/181 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — John P Leubecker

(57) ABSTRACT

A camera system that can be utilized in robotic surgery is presented. In particular, a method of setting a light level in a camera in a robotic system includes determining a location of at least one instrument end effectors within a field-of-view of the camera; determining a region-of-interest in the field-of-view based on the location of the at least one instrument tip; gathering luminance statistics in the region-of-interest; computing a luminance value from the luminance statistics; and adjusting an exposure in response to a comparison of the luminance value with a target luminance value.

20 Claims, 4 Drawing Sheets

(56) References Cited

U.S. PATENT DOCUMENTS

| | | | |
|---|---|---|---|
| 2006/0258938 A1* | 11/2006 | Hoffman et al. | 600/424 |
| 2007/0115372 A1* | 5/2007 | Wu et al. | 348/230.1 |
| 2007/0182845 A1* | 8/2007 | Hunter | 348/362 |
| 2010/0086217 A1* | 4/2010 | Matsuhira | 382/199 |
| 2010/0118159 A1* | 5/2010 | Proca et al. | 348/229.1 |
| 2010/0201842 A1* | 8/2010 | Jung et al. | 348/229.1 |
| 2012/0314124 A1* | 12/2012 | Kaizu et al. | 348/362 |
| 2014/0194896 A1* | 7/2014 | Frimer et al. | 606/130 |

* cited by examiner

AUTO EXPOSURE OF A CAMERA IN A SURGICAL ROBOT

RELATED APPLICATIONS

This application claims priority to U.S. Provisional Application Ser. No. 61/681,090, filed on Aug. 8, 2012, which is herein incorporated by reference in its entirety.

TECHNICAL FIELD

Embodiments of the present invention are related to robotic surgery and, in particular, to operation of a camera utilized in robotic surgery.

DISCUSSION OF RELATED ART

Minimally invasive surgery (MIS) (e.g., endoscopy, laparoscopy, thoracoscopy, cystoscopy, and the like) allows a patient to be operated upon through small incisions by using a camera and elongated surgical instruments introduced to an internal surgical site. The surgical site often comprises a body cavity, such as the patient's abdomen. The body cavity may optionally be distended using a clear fluid such as an insufflation gas, typically $CO_2$. In traditional minimally invasive surgery, the surgeon manipulates the tissues by using hand-actuated end effectors of the elongated surgical instruments while viewing the surgical site on a video monitor.

One or more cannulas may be passed through small (generally 7 cm or less) incisions or a natural body orifice to provide entry ports for the minimally invasive (e.g., endoscopic, laparoscopic, and the like) surgical instruments, including a camera instrument (e.g., endoscope, laparoscope, and the like). A surgeon is able to perform surgery by manipulating the surgical instruments externally to the surgical site under the view provided by the camera instrument.

It is typical to provide several cannulas for a minimally invasive surgical procedure. Such a system is the da Vinci® system sold by Intuitive Surgical. Generally, each cannula will provide access to the surgical site for a single surgical or camera instrument. For example, four cannulas may be provided with one cannula being used to introduce a camera instrument and the remaining three cannulas being used to introduce surgical instruments. Other approaches involve the use of a single incision and cannula (or grouping of cannulas), such as procedures performed using Single-Site™ instrumentation from Intuitive Surgical. However, such approaches still incorporate a camera instrument to allow the surgeon to visualize the operating area.

In either case, the camera instrument is the surgeon's view of the operating arena. If the surgical area is not clearly visible to the surgeon, then the surgical procedure may be more difficult for the surgeon to perform. Therefore, there is a need to develop systems for better viewing of the surgical area.

SUMMARY

In accordance with aspects of the present invention, a method of adjusting an exposure for an imaging system, comprising: determining a location of at least one instrument end effector within a field-of-view of the camera; determining a region of interest in the field-of-view based on the location of the at least one instrument end effector; gathering luminance statistics in the region of interest; computing a measured luminance value from the luminance statistics; and adjusting the exposure in response to a comparison of the measured luminance value with a target luminance value.

These and other embodiments are further discussed below with respect to the following figures.

DETAILED DESCRIPTION

Figure 1A:
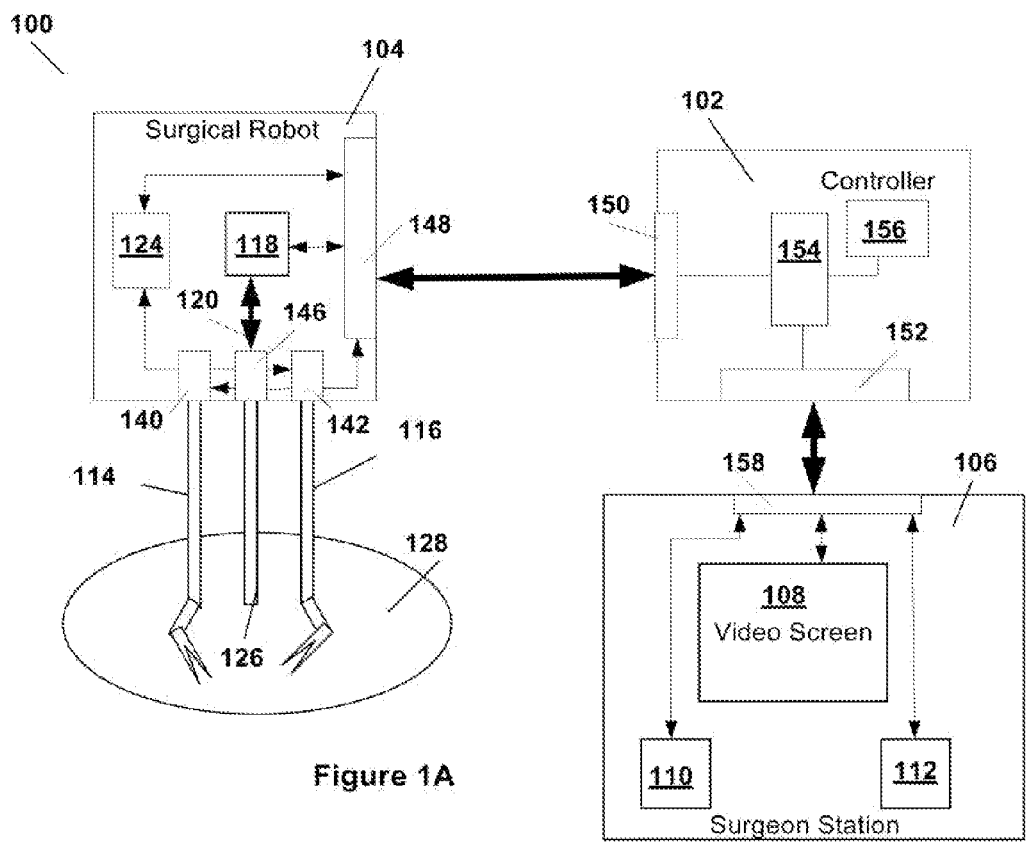
FIG. 1A illustrates robotic surgical system according to some embodiments of the present invention.

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Further, this description's terminology is not intended to limit the scope of the invention. For example, spatially relative terms—such as "beneath", "below", "lower", "above", "upper", "proximal", "distal", "horizontal", "vertical" and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. In addition, to avoid unnecessary repetition in the following description, one or more features shown and described in association with one embodiment may be incorporated into other embodiments unless specifically described otherwise, unless the one or more features would make an embodiment non-functional, or unless two or more of the features provide conflicting functions.

Surgical robots and other minimally invasive surgical techniques often utilize a camera system in order to view the surgical area. Most cameras have to adjust image-processing parameters for a given scene. For example, to accurately capture image detail, a camera system adjusts for different light levels in the field-of-view. This is often accomplished using a process called auto exposure. Auto exposure consists of two steps: (1) determining the current light level in the field-of view and (2) adjusting the exposure time of the camera to properly capture the current scene light level with the camera. However, there are often problems determining the areas in the image where the light levels are monitored in order to determine the exposure times of the camera. Many ad-hoc techniques have been utilized to determine the best image locations to gather the light statistics and ultimately drive the exposure time of the camera. One common technique is to simply define a static region in the image, usually around the center of the field-of-view of the camera. Another common technique is to divide the field-of-view into multiple windows, often disjointed regions, and to either include or discard a window from the light statistics computation based on certain statistical analysis of the windows. Such an algorithm may, for example, exclude one window because it is fully saturated and therefore does not give a good representation of the light level. These window-based algorithms may also weight the contribution of each window for the final light statistics computation. Specifically, windows in the center of the field-of-view can be given a higher weight than windows at the edge of the field-of-view.

The drawbacks of these common techniques (and all known techniques) are that they are essentially guessing where in the field-of-view a viewer, the surgeon, of the image is most likely looking. The static region technique simply assumes the viewer is always looking in the center of the image. This assumption fails badly in a surgical system when the surgeon needs to move the tools to the side of the image to accomplish some task. The window-based technique is a bit better in that fixed windows are selected to be what are thought the most important windows. The technique is still making guesses regarding where the viewer will actually be looking. A situation can easily arise where a window is excluded for some reason (like the light level is too high), but where this window is also the region that the viewer is most interested in viewing.

Some embodiments of the present invention provide methods for determining the image region to drive a camera's auto-exposure algorithm utilizing a known location of the surgical instruments in the field-of-view. The region in which the current light level is determined, the region-of-interest (ROI), can be defined as the area in the field-of-view where a surgeon will most likely be looking. Statistics on the light level can be extracted from the ROI and those statistics utilized to drive the auto-exposure algorithm.

Some embodiments of the present invention work well with surgical systems that track the spatial location of the end effectors of the surgical instruments that are inserted into the surgical area. The spatial location of the end effectors, specifically the area between the end effectors of multiple surgical instruments, is the area in the field-of-view where the surgeon is most likely to be focused. Therefore, in accordance with some embodiments of the present invention, the known location of the end effectors of the surgical instruments is utilized to determine the ROI that is utilized to perform statistics utilized to control the exposure. The ROI can then be continually adjusted when the surgical instruments are moved around the field-of-view by the surgeon.

FIG. 1A illustrates an example robotic surgical system 100 according to some embodiments of the present invention. System 100 includes a surgical robot 104, a controller 102, and a surgical station 106. Surgical robot 104 includes electromechanical drivers 140 and 142 to manipulate surgical instruments 114 and 116, respectively. Surgical instruments 114 and 116 may also be mounted on surgical arms that themselves have joints that are manipulated by electromechanical drivers in robot 104. Although surgical instruments 114 and 116 are illustrated in FIG. 1A, there may be any number of surgical instruments that are simultaneously operated through electromechanical drivers by surgical robot 104.

Further, surgical robot 104 may include a camera instrument 126 coupled to a camera 118 through coupler 120, which may be optical fiber or electronic connections. Camera instrument 126 may also be mounted an a surgical arm and its position manipulated by electromechanical driver 146 in robot 104. In some embodiments, camera 118 may be mounted on a robot arm to which camera instrument 126 is mounted and controlled. As shown in FIG. 1A, surgical instruments 114 and 116 along with camera instrument 126 are inserted into a surgical area 128. Each of instruments 114, 116, and 126 may be inserted through a separate port, as is accomplished in multi-port surgery. Alternatively, instruments 114, 116, and 126 may be inserted through a single port as is performed in a single port surgical system.

As is further illustrated in FIG. 1A, camera 118 and electromechanical drivers 140, 142, and 146 are coupled through electronics 148 to controller 102. Electronics 148 may include one or more processors and includes interface electronics to communicate with controller 102. Electronics 148 receive signals from controller 102 and provides input signals to camera 118, drivers 140, 142, and 146, and other components of robot 104. Further, electronics 148 can receive signals from various sensors 124 in robot 104 that provide information regarding the position of instruments 114, 116, and 126 in surgical area 128. Sensors 124 are distributed throughout robot 104 and can be included, for example, in each of drivers 140, 142, and 146. Sensors 124 provide information regarding the disposition of each of instruments 114, 116, and 126, including the spatial location and disposition of end effectors of instruments 114 and 116 and the spatial location and disposition of camera instrument 126. Data received from sensors 124 can be communicated with controller 102.

Controller 102 provides signals that control surgical robot 104, including camera 118 and electromechanical drivers 140, 142, and 146. Controller 102 also receives signals from sensors 124 on surgical robot 104 that provides information regarding the disposition of instruments 114, 116, and 126 in surgical area 128. As shown in FIG. 1A, controller 102 includes one or more processors 154 coupled to data storage 156. Data storage 156 can be any volatile or non-volatile memory and may include media such as hard drives or other storage medium. Processors 154 are coupled to data interface 150 for communication with surgical robot 104 and to data interface 152 for communication with surgeon station 106.

Processor 154 executes instructions stored in controller 156 to control surgical robot 104. In particular, processor 154 directs all of the drivers, including drivers 140, 142, and 146, in surgical robot 104 in order to position and manipulate instruments 114, 116, and 126. Additionally, controller 154 receives information from sensors in surgical robot 104 that monitors and reports on the condition and position of instruments 114, 116, and 126. As such, controller 102 tracks and determines the positions and orientation of each of instruments 114, 116, and 126, receives instructions from surgeon station 106, determines the motions of instruments 114, 116, and 126, and provides signals to surgical robot 105 to implement those motions. Further, controller 102 can control aspects of camera 118, as is further discussed below.

Surgeon station 106 includes a video display 108 and manipulators 110 and 112. A surgeon can view surgical area 128 on video screen 108 and manipulate instruments 114 and 116 utilizing manipulators 110 and 112. Signals from manipulators 110 and 112 are provided to controller 102 and are utilized by processors 154 to determine the motion of instruments 114 and 116. The video output from camera 118 is provided on video screen 108 so that the surgeon can view the surgical procedure. In some embodiments, camera 118 may be a stereo camera and video screen 108 a stereo viewer.

Figure 1B:
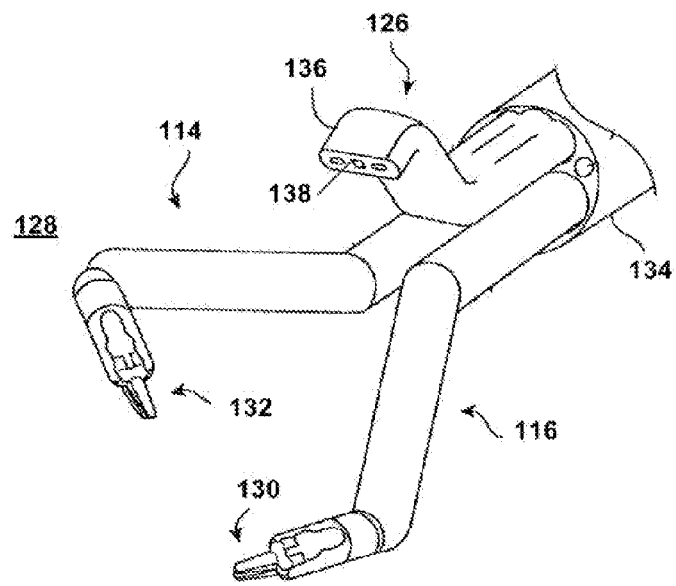
FIG. 1B illustrate instruments utilized in surgery in a single-port surgical system.

FIG. 1B illustrates the end effectors of instruments 114, 116, and 126 that are inserted within surgical area 128. In the example shown in FIG. 1B, system 100 is illustrated as a single port system, although it is understood that a multi-port system can result in similar relative configurations of camera 126 and instruments 114 and 116. Therefore, instruments 114, 116, and 126 are inserted through a single cannula 134. In a multi-port system, each of instruments 114, 116, and 126 could be inserted through its own cannula 134. Cannula 134 is inserted through the body wall adjacent to surgical area 128. As illustrated in FIG. 1B, instruments 114 and 116 can each include end effectors (or tips) 132 and 130, respectively. End effectors 132 and 130 can be positioned within surgical instrument 128 and manipulated, as discussed above, in accordance with inputs from a surgeon. Camera instrument 126 includes a camera head 136 which includes optical ports 138 that provide light to surgical area 128 and receive light from surgical area 128. The light from surgical area 128 may be transported to optical detectors in camera 118 through optical fiber in coupler 120 or the optical detectors may be included in camera head 126 and coupler 120 may be electronic. As shown in FIG. 1B, camera head 136 can also be manipulated and positioned to provide the surgeon with a useful view of surgical area 128. As noted above, in various other embodiments, camera 118 can be positioned at camera head 136 (e.g., with optical ports 138 including one or more lenses for camera 118). Camera head 136 may include detector arrays for detection of light represented by camera 118 and may be a stereo viewer.

Figure 2:
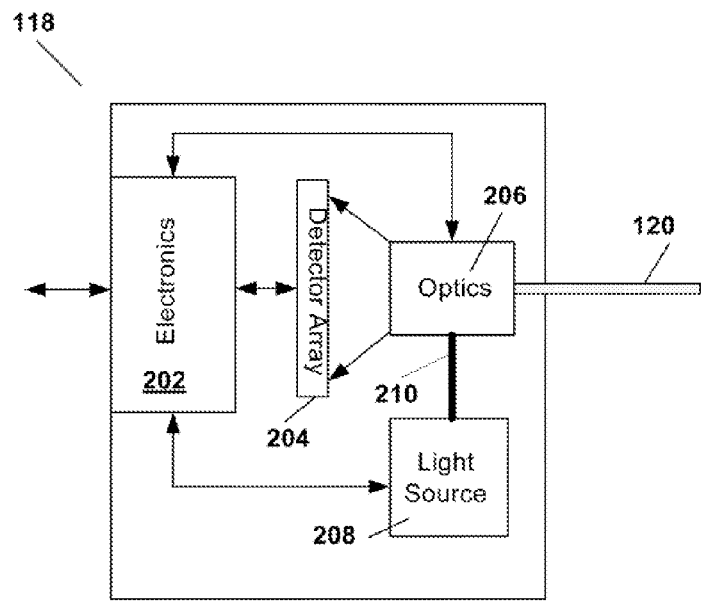
FIG. 2 illustrates a camera instrument according to some embodiments of the present invention.

FIG. 2 shows a block diagram illustration of an example of camera 118. As shown in FIG. 2, camera 118 includes a detector array 204 that is coupled through optics 206 to receive light from optical fiber in connector 120. Camera 118 further includes a light source 208 that provides light into optical fiber of connector 120 through optics 206. In some embodiments, optical fiber 120 can include separate fibers for collecting light from surgical area 128 and delivering light to surgical area 128. Light from light source 208 is utilized to illuminate surgical area 128. Reflected light from surgical area 128 is collected at camera head 136 and focused to form an image of surgical area 128 on detector array 204. Optics 206, light source 208, and detector array 204 are controlled by electronics 202. Electronics 202 may include a processor and memory in order to perform the functions of camera 118. Those functions may include, for example, auto focus functions, auto exposure, exposure times, and data collection. Detector array 204 can be an array of pixels of any size. Common array sizes include, for example, 1280×1024, 800× 600, or 640×512. In some embodiments, stereo images may also be utilized. Although detector array 204 can detect any wavelength of radiation (for example infrared radiation or near infrared radiation), in most cases, the pixels can be RGB detectors (i.e., detector array 204 provides three-color data as R, G, and B where R provides a value for the light intensity of red light, G provides a value for the light intensity of green light, and B provides a value for the light intensity of blue light). In some embodiments, R, G, and B pixels can be arranged in a Bayer pattern. Data can be read from detector array by electronics 202 with any accuracy, for example 12 bit accuracy where an individual pixel (which can be a red, green, or blue detector) can be represented by 12-bit words. Other arrangements of detectors and other resolutions can also be utilized. For example, in some embodiments, optics 206 may be one or more lenses or windows that transmit reflected light from surgical area 128 onto detector array 204 (eliminating the need for optical fiber 120). As discussed above, in embodiments detector array 204 and a portion of optics 206 may be mounted in camera head 136.

In practice, light intensity on the detectors in detector array 204 is integrated over an exposure time. The three-valued RGB pixel data is then read from detector array 204 at a particular frame rate. The image represented by that pixel data can be transmitted by electronics 202 to controller 102, which can display the image on video screen 108 of surgeon station 106. Electronics 202 can include processors that execute auto-focus, auto-exposure, and other common functions associated with the operation of digital camera 118.

Figure 3A:
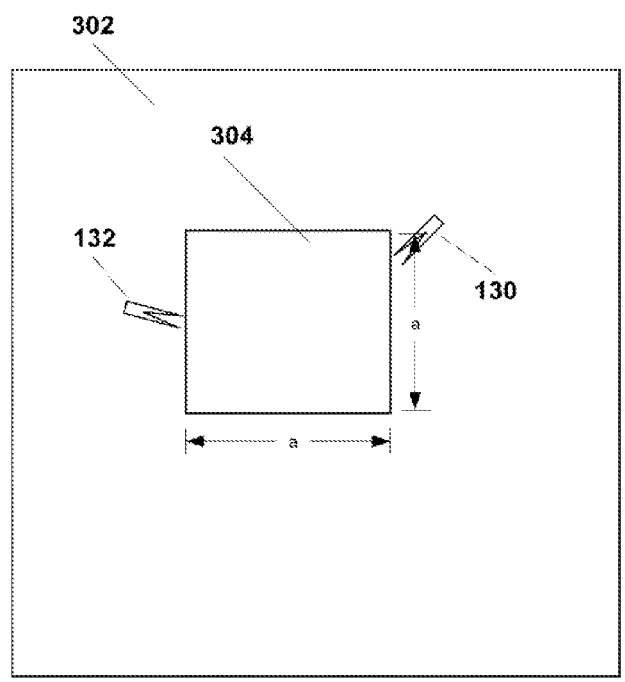
FIGS. 3A, 3B, and 3C illustrate region-of-interest determination according to some embodiments of the present invention.

FIG. 3A illustrates the field of view 302 of the image provided on detector array 204 by camera head 136. Field-of-view 302 represents the area recorded on detector array 204. In conventional systems, the image of that area would have a brightness that is determined by the intensities of the reflected light captured by camera head 136. Therefore, a particularly bright reflection that is utilized to determine the exposure time may result in an image in electronics 202 that is too dim in some aspects for the surgeon to utilize.

Figure 3B:
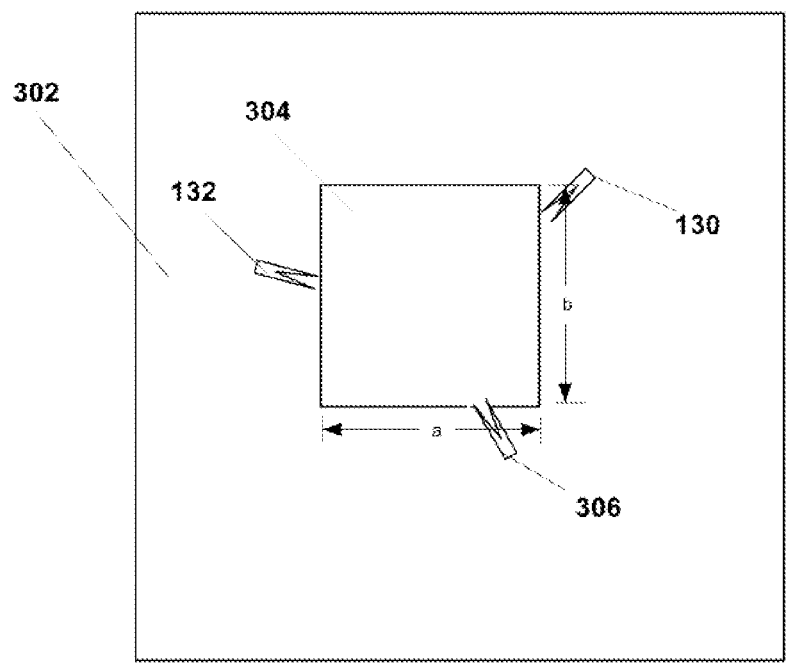
Figure 3C:
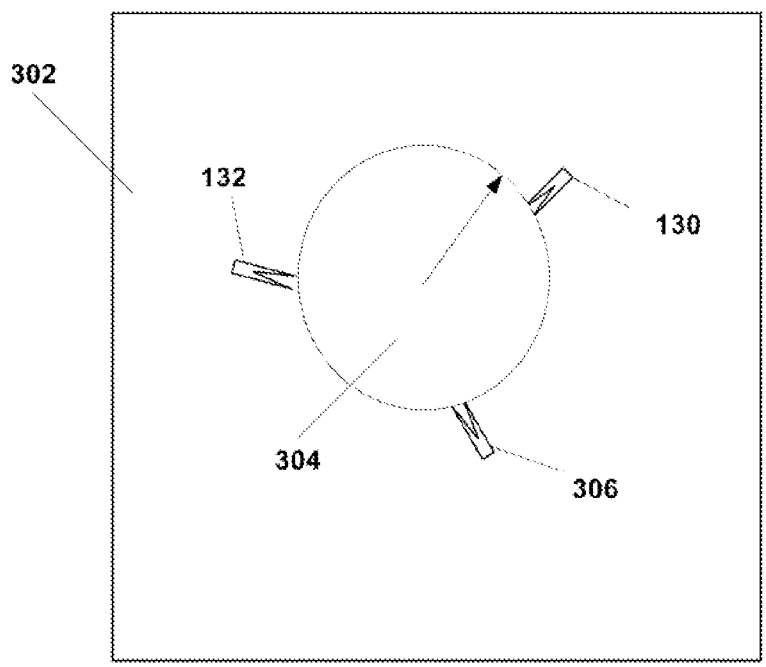

As shown in FIG. 3A, a ROI 304 can be defined by the positions of end effectors 132 and 130. The surgeon's interest is highly likely to be directed to the portion of surgical region 128 that is between end effectors 132 and 130. This ROI is illustrated as ROI 304 in FIG. 3A. ROI 304 can be determined by the location of end effectors 130 and 132. Note that although the distal tips of end effectors 130 and 132 would typically be used to define ROI 304, in various embodiments, ROI 304 can be based on end effectors 130 and 132 as a whole (e.g., the envelopes, centroids, or predetermined points on end effectors 130 and 132). As shown in FIG. 3B, if there are more than two end effectors (end effectors 130, 132, and 306 are illustrated in FIG. 3B), then ROI 304 can be determined by the location of some or all of the end effectors. Although ROI 304 is illustrated as rectangular in FIGS. 3A and 3B, ROI 304 can be defined in any shape. FIG. 3C illustrates ROI 304 as circular or elliptical, for example. In some embodiments, ROI 304 can be set over a larger area which includes end effectors 130 and 132 (e.g., a region having a square, rectangular, circular, elliptical, or other shape that overlaps the locations of end effectors 130 and 132). In other embodiments, ROI 304 can be a region between, but not extending all the way to, end effectors 132 and 130 (e.g., a region having a square, rectangular, circular, elliptical, or other shape that is between but does not include the locations of end effectors 130 and 132). Although rectangular or elliptical shapes for ROI 304 are illustrated in FIGS. 3A, 3B, and 3C, as noted above, other geometric shapes (for example triangles) can also be utilized.

Note that in various embodiments, the size and/or shape of ROI 304 can change or remain constant in response to the movement of end effectors 130 and 132. For example, in some embodiments, ROI 304 can be resized as end effectors 130 and 132 move relative to one another (e.g., ROI 304 increases or decreases in size as end effectors 130 and 132 move farther apart or closer together, respectively). In other embodiments, ROI 304 can maintain a constant size as end effectors 130 and 132 move relative to one another.

Figure 4:
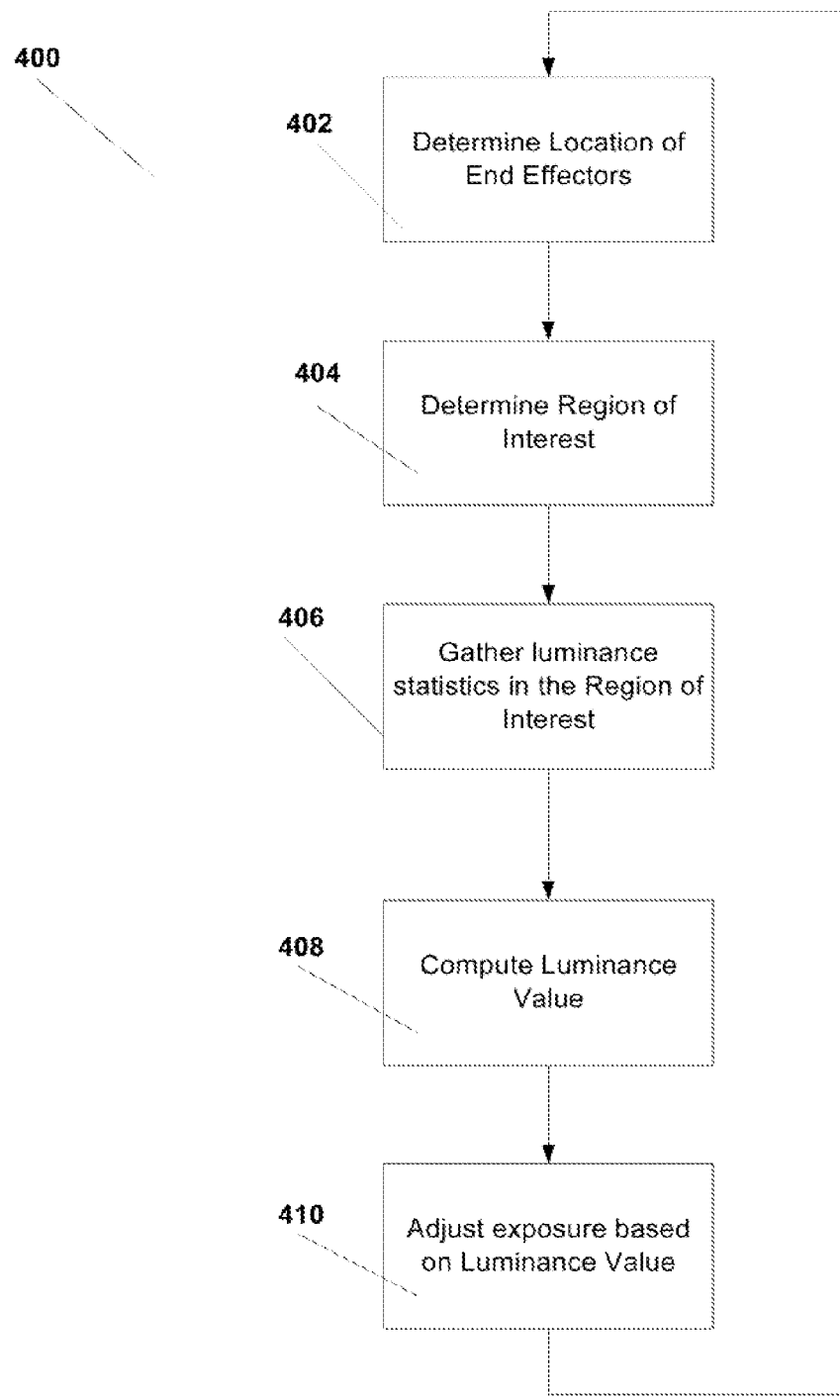
FIG. 4 illustrate a method of controlling the exposure for images within the region of interest according to some embodiments of the present invention.

FIG. 4 illustrates a method 400 of operating camera 118 such that viewing of features within ROI 304, the surgeon's most probable area of interest, is substantially clear for the surgeon at surgeon station 106. Although video screen 108 may present a large portion of field of view 302 of camera 118, the light level in ROI 304 can be set to best highlight structures in ROI 304. Method 400 may be executed anywhere in system 100. For example, method 400 may be executed by processor 154 of controller 102. In some embodiments, method 400 may be at least partially executed by electronics 202 in camera 118. Further, the surgeon at surgeon station 106 may control some aspects of method 400. Method 400 may be performed by one or more processors (e.g. processors 154 of controller 102 or within camera 118) executing instructions, may be performed by circuits (e.g. in controller 102 or within camera 118), or may be performed by a combination of processors and circuits. Instructions for processors may be stored in memory 156, camera 118, or on a computer readable medium (e.g., hard drive, optical disk, flash card, etc.).

As shown in FIG. 4, in step 402 method 400 determines the location of end effectors within the field of the camera. Controller 102 provides the physical locations of each of the end effectors, for example end effectors 130 and 132, to method 400. Controller 102 also provides the physical location and orientation of camera head 136. Consequently, method 400 can determine the location of each of end effectors 130 and 132 as viewed in field-of-view 302. This can be accomplished by mapping the physical locations of each of the end effectors into the field-of-view defined by the orientation of the camera. In other embodiments, end effectors 130 and 132 can be directly identified within field-of-view 302 (e.g., via known markings (such as fiducials or other targets) or visual recognition (such as pattern matching or feature identification)).

In some embodiments, controller 102 can recognize the image of end effectors 130 and 132 in field-of-view 302 in order to assist in determining a more precise location of the end effectors from the physical positions provided from sensors 124. For example, controller 302 may place the location of end effectors 130 and 132 approximately in field-of-view 302 and then utilize the image from camera 118 to finalize the location of end effectors 130 and 132 in field-of-view 302.

In step 404, method 400 determines the region-of-interest, ROI 304. ROI 304 is determined by the location of the end effectors. For example, in FIG. 3A, ROI can be a square with side length a where the side length a is determined by the distance between end effectors 130 and 132. For example, the side length a can be set to the distance between end effectors 130 and 132. Alternatively, the side length a can be set to be larger than the distance between end effectors 130 and 132 by a predetermined amount. ROI 304 can be determined by any shape that spans at least a portion of the region between the end effectors.

In FIG. 3B, ROI can be a rectangle with side lengths a and b. Length b can be determined by the distance between end effectors 130 and 360, the vertical separation between end effectors 306 and 132 being less than the vertical separation between end effectors 130 and 306, and length a can be determined by the distance between end effectors 130 and 132, the horizontal separation between end effectors 132 and 306 being less than the horizontal separation between end effectors 132 and 130. As shown in FIG. 3B, ROI 304 is set to encompass each of end effectors 130, 132, and 306. In a case where end effector 306 is absent, then the side length b can be set to be a value determined by the side length a. The length of a and b can, therefore, be determined by the horizontal and vertical separation between all of the effectors. If there are multiple effectors, the largest distance between effectors in the horizontal and vertical direction can be utilized. In some embodiments, if the lengths a or b fall below a minimum length, then a or b can be set to a predetermined minimum length. In other embodiments, if the lengths a or b exceed a maximum length, then a or b can be set to a predetermined maximum length.

FIG. 3C illustrates a circular ROI 304 where the radius r of the circle is determined to include the space between end effectors 130, 132, and 306. In general, ROI 304 is set to cover the area between all of the end effectors (end effectors 130, 132, and 306, for example). In some embodiments, the center of the circular ROI 304 can be determined to be the average location of all of the effectors and the radius r set to be the largest distance from the circle center to each of the effectors. Examples of some methods of determining ROI 304 is provided in this disclosure, however any other definition of ROI 304 that depends on the locations of the end effectors (e.g., end effectors 130, 132, and 306) can be utilized. ROI 304 may or may not include end effectors, or may include some end effectors and not others.

In step 406, luminance statistics are gathered in ROI 304. As discussed above, pixels in detector array 204 are represented by values R (red), G (green), and B (blue). In step 406, pixels that fall within ROI 304 can be averaged so that an average R ($\overline{R}$) an average G ($\overline{G}$) and an average B ($\overline{B}$) can be determined within ROI 304. From the average values $\overline{R}$, $\overline{G}$, and $\overline{B}$, a luminance value can be computed as $$L = \alpha \vec{R} + \beta \vec{G} + \gamma \vec{B},$$

where $\alpha$, $\beta$, and $\gamma$ are parameters that determine the relative weighting for each of R, G, and B to provide for the luminance. Since the color green contributes the most to human perception while blue contributes the least, in some embodiments, $\alpha$, $\beta$, and $\gamma$ can be chosen based on human perception. For example, the following parameter set that reflects human perception can be utilized: $\alpha=0.2126$, $\beta=0.7152$, and $\gamma=0.0722$. Other sets of parameters $\alpha$, $\beta$, and $\gamma$ can also be utilized depending on the camera and other circumstances.

In step 410, the exposure is adjusted in response to the luminance value. If L is greater than a target luminance, then the exposure is reduced. If L is less than a target luminance, then the exposure is increased. The target luminance value can be adjusted by the surgeon. In some embodiments, however, the target luminance can, for example, be set as a percentage grey average, for example 18% grey. Therefore, the target luminance can be set, for a 12 bit camera, to 4095*0.18, the representation for luminance in a 12 bit camera is between 0 and 4095. In some embodiments, the target luminance L can be adjusted by the surgeon at surgeon station 106. The exposure can be adjusted by adjusting one or more camera parameters.

The exposure can be adjusted in a number of ways. For example, the light intensity of light source 208 can be adjusted. Alternatively, the gain of detector array 204 can be adjusted. The gain can be adjusted digitally in electronics 202, but such amplification may also amplify the noise. Further, the sensitivity of detector array 204 can be modified. In some embodiments, exposure time of detector array 204 can be adjusted. Additionally, in some embodiments a variable aperture can be adjusted to affect the light levels. In some cases, a combination of these adjustments can be utilized to adjust the light levels in ROI 304.

Since there is typically a delay between the instruction for an adjustment of the exposure and its effect in field-of-view 302, small steps may be utilized in making adjustments. For example, there may be several frames of delay between the instruction for adjustment and the time when the adjustment is actually implemented and show an effect. For example, in embodiments where the exposure time is utilized to adjust the light levels, the exposure time can be adjusted according to the following:

$$ET_{j+1} = ET_j + \delta(L - \text{Target } L),$$

where δ is chosen to make adjustments appropriately in camera 118 based on the delay between the instruction for an adjustment. Other methods of changing brightness (e.g., adjustment of gain, adjustment of light source 208, or other adjustment) can generally follow a similar adjustment equation. In some embodiments, adjustments can be made in light of historical responses to previous adjustments.

In some embodiments, camera 118 may be a fixed focus camera that is adjusted for system 100. Where camera 118 provides an auto-focus function, in some embodiments controller 302 can direct camera 118 to confine the auto-focus to objects within ROI 304.

Embodiments of the invention have been described above with respect to surgical robots. However, embodiments of the invention can have practical application in other robotic system where the physical location and orientation of instruments that are manipulated by the robot are tracked and available. Such systems may provide the operator with a view where the light intensity of the area between the instruments in the field-of-view is monitored and adjusted.

The above detailed description is provided to illustrate specific embodiments of the present invention and is not intended to be limiting. Numerous variations and modifications within the scope of the present invention are possible. The present invention is set forth in the following claims.

What is claimed is:

1. A method of adjusting an exposure for an imaging system, comprising:
   determining a location for each of a plurality of instrument end effectors within a field-of-view of a camera by receiving a physical location of the instrument end effector, a physical location of the camera, and mapping the physical location of the instrument end effectors into the field-of-view determined by the physical location of the camera;
   determining a region of interest in the field-of-view based on the location for each of the plurality of instrument end effectors in the field-of-view of the camera;
   gathering luminance statistics for the region of interest;
   computing a measured luminance value from the luminance statistics; and
   adjusting the exposure in response to a comparison of the measured luminance value with a target luminance value.

2. The method of claim 1, wherein the location for each of the plurality of instrument end effectors is further refined utilizing an image in the field of view.

3. The method of claim 1, wherein the plurality of instrument end effectors includes at least two end effectors and determining the region of interest includes defining the region of interest at least partially between the at least two end effectors.

4. The method of claim 1, wherein the plurality of instrument end effectors includes at least two end effectors and determining the region of interest includes defining a rectangular region of interest with side dimensions that span at least a portion of an area between the at least two end effectors.

5. The method of claim 1, wherein the plurality of instrument end effectors includes at least two end effectors and determining the region of interest includes defining a triangular region of interest with side dimensions that span at least a portion of an area between the at least two end effectors.

6. The method of claim 1, wherein the plurality of instrument end effectors includes at least two end effectors and determining the region of interest includes defining a circular region of interest with radius large enough that the circular region of interest spans the region between the at least two end effectors.

7. The method of claim 1, wherein gathering luminance statistics within the region-of-interest includes averaging the intensities of green light to acquire an average green intensity, averaging the intensities of red light to acquire an average red intensity, and averaging the intensities of blue light to acquire an average blue intensity.

8. The method of claim 1, wherein the luminance value is a weighted sum of the average green, the average red, and the average blue intensities.

9. The method of claim 1, wherein adjusting the exposure includes adjusting at least one of an exposure time, a light source intensity, a gain, a sensitivity, and a variable aperture.

10. A surgical system, comprising:
    a surgical robot that manipulates a plurality of instrument end effectors and a camera instrument within a surgical area in response to received signals;
    a surgeon station that displays images received from the camera instrument; and
    a controller coupled between the surgical robot and the surgeon station to provide images from the camera instrument to the surgeon station and the received signals to the surgical robot, the controller further,
        determining a location of each of the plurality of instrument end effectors within a field-of-view of the camera by receiving a physical location of the instrument end effector, a physical location of the camera, and mapping the physical location of the instrument end effectors into the field-of-view determined by the physical location of the camera;
        determining a region of interest in the field-of-view based on the location of the plurality of instrument end effectors in the field of view;
        gathering luminance statistics in the region of interest;
        computing a measured luminance value from the luminance statistics; and
        adjusting an exposure in response to a comparison of the measured luminance value with a target luminance value.

11. The system of claim 10, wherein the surgical robot includes one or more sensors that provide signals related to the location of the plurality of instrument end effectors to the controller.

12. The system of claim 10, wherein the location of the each of the plurality of instrument end effectors is further refined by utilizing an image in the field of view.

13. The system of claim 10, wherein the plurality of instrument end effectors includes at least two end effectors and determining the region of interest includes defining the region of interest at least partially between the at least two end effectors.

14. The system of claim 10, wherein the plurality of instrument end effectors includes at least two end effectors and determining the region of interest includes defining a rectangular region of interest with side dimensions that span at least a portion of an area between the at least two end effectors.

15. The system of claim 10, wherein the plurality of instrument end effectors includes at least two end effectors and determining the region of interest includes defining a triangular region of interest with side dimensions that span at least a portion of an area between the at least two end effectors.

16. The system of claim 10, wherein the plurality of instrument end effectors includes at least two end effectors and determining the region of interest includes defining a circular region of interest with radius large enough that the circular region of interest spans the region between the at least two end effectors.

17. The system of claim 10, wherein gathering luminance statistics includes averaging the intensities of green light, intensities of red light, and intensities of blue light for pixels within the region-of-interest to acquire average green, average red, and average blue intensities.

18. The system of claim 17, wherein the luminance value is a weighted sum of the averaged green, the average red, and the average blue intensities.

19. The system of claim 10, wherein adjusting the exposure includes adjusting at least one of an exposure time, a light source intensity, a gain, a sensitivity, and a variable aperture.

20. An apparatus, comprising a non-transitory computer readable medium storing instructions for:
   determining a location of a plurality of instrument end effectors within a field-of-view of a camera in a surgical system by receiving a physical location of the instrument end effector, a physical location of the camera, and mapping the physical location of the instrument end effectors into the field-of-view determined by the physical location of the camera;
   determining a region of interest in the field-of-view based on the location of the plurality of instrument end effectors;
   gathering luminance statistics in the region of interest;
   computing a measured luminance value from the luminance statistics; and
   adjusting an exposure in response to a comparison of the measured luminance value with a target luminance value.

* * * * *